(12) United States Patent
Hasegawa et al.

(10) Patent No.: US 8,993,344 B2
(45) Date of Patent: Mar. 31, 2015

(54) METHOD FOR DETECTING PROZONE PHENOMENON, ANALYSIS METHOD, DEVICE FOR DETECTING PROZONE PHENOMENON, AND ANALYSIS DEVICE

(75) Inventors: Hironori Hasegawa, Kyoto (JP); Kyouichi Ohshiro, Kyoto (JP); Satoshi Fukunaga, Kyoto (JP)

(73) Assignee: Arkray, Inc., Kyoto (JP)

( * ) Notice: Subject to any disclaimer, the term of this patent is extended or adjusted under 35 U.S.C. 154(b) by 275 days.

(21) Appl. No.: 13/258,374

(22) PCT Filed: Jul. 16, 2010

(86) PCT No.: PCT/JP2010/062066
§ 371 (c)(1),
(2), (4) Date: Sep. 21, 2011

(87) PCT Pub. No.: WO2011/016326
PCT Pub. Date: Feb. 10, 2011

(65) Prior Publication Data
US 2012/0015450 A1    Jan. 19, 2012

(30) Foreign Application Priority Data
Aug. 7, 2009 (JP) ................... 2009-185298

(51) Int. Cl.
*G01N 33/53* (2006.01)
*G01N 33/557* (2006.01)
*G01N 33/558* (2006.01)

(52) U.S. Cl.
CPC .......... *G01N 33/557* (2013.01); *G01N 33/5306* (2013.01); *G01N 33/558* (2013.01)
USPC ........................................................ 436/501

(58) Field of Classification Search
CPC ................................................. G01N 33/5306
See application file for complete search history.

(56) References Cited

U.S. PATENT DOCUMENTS

| 6,183,972 B1* | 2/2001 | Kuo et al. ........... 435/7.1 |
| 2003/0100128 A1* | 5/2003 | Kenjyou et al. ............. 436/518 |
| 2004/0029177 A1 | 2/2004 | Nadaoka et al. ............. 435/7.1 |
| 2006/0246601 A1 | 11/2006 | Song et al. |
| 2007/0243559 A1* | 10/2007 | Gunzer et al. ............ 435/7.1 |
| 2011/0076781 A1* | 3/2011 | Liu et al. ................. 436/501 |

FOREIGN PATENT DOCUMENTS

| EP | 0987551 A2 | 3/2000 | |
| EP | 1416276 A1 | 5/2004 | |
| JP | 08-278305 | 10/1996 | ........... G01N 33/543 |
| JP | 2002-122599 | 4/2002 | ........... G01N 33/543 |

(Continued)

OTHER PUBLICATIONS

International Search Report for PCT/JP2010/062066 (mailed Aug. 17, 2010).

(Continued)

*Primary Examiner* — Bao Thuy L Nguyen
*Assistant Examiner* — Gary E Hollinden
(74) *Attorney, Agent, or Firm* — Morgan, Lewis & Bockius LLP

(57) ABSTRACT

Provided is a prozone phenomenon detecting method, by which generation of a prozone phenomenon can be detected even when a conventional specimen analysis tool is used, and examinations using an immunochromatography method and the like can be performed efficiently.

10 Claims, 5 Drawing Sheets

(56) References Cited

FOREIGN PATENT DOCUMENTS

| | | | | |
|---|---|---|---|---|
| JP | 2002-122599 A1 | 4/2002 | | |
| JP | 3644780 | 2/2005 | ........... | G01N 33/543 |
| JP | 3726082 B2 | 12/2005 | | |
| JP | 06-250787 | 9/2006 | ........... | G01N 33/543 |
| JP | 2006-250787 A1 | 9/2006 | | |
| WO | WO 03/014740 | 2/2003 | ........... | G01N 33/543 |

OTHER PUBLICATIONS

Extended European Search Report issued in corresponding European Patent Application No. 10806326.4 dated Dec. 3, 2012.

Office Action issued in corresponding European Patent Application No. 10806326.4 dated May 13, 2014.

* cited by examiner

METHOD FOR DETECTING PROZONE PHENOMENON, ANALYSIS METHOD, DEVICE FOR DETECTING PROZONE PHENOMENON, AND ANALYSIS DEVICE

CROSS-REFERENCE TO RELATED APPLICATION

This application is a 371 filing based on PCT/JP2010/062066, filed Jul. 16, 2010, which claims priority to Japanese Application No. JP2009-185298, filed Aug. 7, 2009, all of which are hereby incorporated by reference in their entirety.

TECHNICAL FIELD

The present invention relates to a method for detecting a prozone phenomenon, an analysis method, a device for detecting a prozone phenomenon, and an analysis device.

BACKGROUND ART

In recent years, in diagnoses in the medical field, specimen analysis tools for detecting pathogens such as bacteria and viruses or determining the presence or absence of pregnancies are in widespread use. Among these specimen analysis tools, a specimen analysis tool utilizing an immunochromatography method is used widely because it enables detections to be conducted easily and rapidly. The principle of detection by the immunochromatography method performed using the specimen analysis tool is as follows, for example. First, a specimen analysis tool formed of a porous base material in which immobilized antibodies are immobilized on a detection portion of the porous base material is provided. A sample (a specimen) and antibodies labeled with colored particles are added thereto. When antigens as a target component are present in the sample, the labeled antibodies and the immobilized antibodies form complexes via the antigens, whereby the detection portion on the porous base material is colored by the colored particles. The label may be, for example, in addition to the colored particles, a combination of an enzyme and a substrate that is colored by an enzyme reaction. The detection portion generally is in a line form. When coloring is observed, it is regarded that the target component is present in the sample, so that it is determined that the sample is positive. When no coloring is observed, it is regarded that no target component is present in the sample so that it is determined that the sample is negative. In the immunochromatography method, it has been attempted that plural detection portions are provided and a target component in a sample is semiquantitatively detected by observing stepwise coloring (see, for example, JP H8-278305 A).

In the detection of a target component using an immunochromatography method, a prozone phenomenon is generated in the case where the concentration of the target component is high, which is a problem. The prozone phenomenon is a phenomenon in which although the actual concentration of the target component in a sample is high, it is apparently determined that the target component is not present or the concentration thereof is low. FIG. 5 is an illustration showing a relationship between the concentration of antigen and the absorbance (the degree of coloring) in a detection portion in an immunochromatography method. The absorbance is increased with an increase in the concentration of the antigen. However, when the concentration reaches a certain concentration or higher, a phenomenon in which an absorbance cannot be determined (coloring does not occur) is generated. Therefore, for example, when the concentration of antigen is $Z_1$, an absorbance X is detected, and when the concentration of antigen is $Z_2$ in a high concentration region, the same absorbance is also detected because a prozone phenomenon is generated. This phenomenon is caused by the fact that when the excess amount of the target component is present in a sample, the immobilized antibodies are blocked by the target component that has not reacted with labeled antibodies, so that the target component that has reacted with the labeled antibodies cannot be captured by the immobilized antibodies. Therefore, in an analysis, there is a case that a sample with a concentration in the high concentration region is apparently determined as negative (i.e., a false-negative), and it is difficult to distinguish a false-negative from an actual negative. When a false-negative caused by a prozone phenomenon is suspected, it has been required that a sample is diluted as appropriate and then re-examination is performed. On the other hand, it has been proposed to detect a prozone phenomenon that plural types of antibodies, which are different in affinity from one another are used as immobilized antibodies in a specimen analysis tool (see, for example, WO 2003/014740) and stepwise increased amounts of antibodies are applied to the plural detection portions (see, for example, JP No. 3644780).

SUMMARY OF INVENTION

Problem to be Solved by the Invention

In the above-mentioned methods, the specimen analysis tool needs to have a complicated structure. Further, there is a risk that the examination efficiency is reduced because the detection of the generation of a prozone phenomenon cannot be continued until the reaction is completed in a region on the most downstream side of the plural detection portions. These problems may occur not only in an immunoanalytical method utilizing an immunological reaction in which antibodies that specifically bind to antigens as a target component contained in a specimen are used, but also in analysis methods in general using a substance (e.g., a specifically-binding substance) that specifically binds to a target component contained in a specimen.

Hence, the present invention is intended to provide a method for detecting a prozone phenomenon, an analysis method, a device for detecting a prozone phenomenon, and an analysis device, by which generation of a prozone phenomenon can be detected easily even when a conventional specimen analysis tool is used, and examinations using an immunochromatography method and the like can be performed efficiently.

Means for Solving Problem

In order to achieve the aforementioned object, the prozone phenomenon detecting method of the present invention is a method for detecting a prozone phenomenon using a specimen analysis tool containing substances that specifically bind to a target component contained in a sample. The specimen analysis tool includes: a porous base material; a sample supplying portion; a reagent portion; and at least one detection portion. The sample supplying portion, the reagent portion, and the detection portion are arranged on the porous base material from upstream to downstream in a sample moving direction in this order. The reagent portion contains a labeled substance that specifically binds to the target component. The detection portion contains an immobilized substance that specifically binds to the target component. The target component is detected by detecting a complex of the target component, the labeled substance, and the immobilized substance through detection of a label of the labeled substance in the detection portion. The prozone phenomenon detecting method includes at least one of the following processes A and B:

the process A: a process in which detection results obtained in the detection portion are plotted along the sample moving direction, and generation of a prozone phenomenon is detected on the basis of a position of a peak in plots thus obtained; and the process B: a process in which the label is detected at two or more different time points in the detection portion, and generation of a prozone phenomenon is detected on the basis of a magnitude relationship between two or more detection results thus obtained.

The analysis method of the present invention is an analysis method including: an analyzing step; and a prozone phenomenon detecting step. The analyzing step is performed using a specimen analysis tool, and the prozone phenomenon detecting step is performed by the prozone phenomenon detecting method of the present invention. The specimen analysis tool includes: a porous base material; a sample supplying portion; a reagent portion; and at least one detection portion. The sample supplying portion, the reagent portion, and the detection portion are arranged on the porous base material from upstream to downstream in a sample moving direction in this order. The reagent portion contains a labeled substance that specifically binds to the target component. The detection portion contains an immobilized substance that specifically binds to the target component. The target component is detected by detecting a complex of the target component, the labeled substance, and the immobilized substance through detection of a label of the labeled substance in the detection portion.

The prozone phenomenon detecting device of the present invention is used in the prozone phenomenon detecting method of the present invention. The device includes: a section for obtaining detection results in the detection portion; and at least one of the following sections A and B:

the section A: a section for detecting generation of a prozone phenomenon on the basis of a position of a peak in plots obtained by plotting the detection results along a sample moving direction; and the section B: a section for detecting a label at two or more different time points and detecting generation of a prozone phenomenon on the basis of a magnitude relationship between two or more detection results thus obtained.

The analysis device of the present invention is used in the analysis method of the present invention. The analysis device includes: an analysis section; and a prozone phenomenon detecting section. The analysis section detects a target component by detecting a complex of the target component, a labeled substance, and an immobilized substance through detection of a label of the labeled substance in a detection portion of a specimen analysis tool. The prozone phenomenon detecting section is the prozone phenomenon detecting device of the present invention.

Effects of the Invention

According to the present invention, it becomes possible to easily detect generation of a prozone phenomenon even when a conventional specimen analysis tool is used and becomes possible to efficiently perform examinations using an immunochromatography method and the like in which an analysis is performed using a specifically-binding substance. Thus, it can be said that the present invention is very useful in an analysis field, a clinical field, and the like.

BRIEF DESCRIPTION OF DRAWINGS

FIG. 1A shows a result with respect to a sample having a CRP concentration of 60 mg/100 mL. FIG. 1B shows a result with respect to a sample having a CRP concentration of 6.5 mg/100 mL.

BEST MODE FOR CARRYING OUT THE INVENTION

Figure 1A:
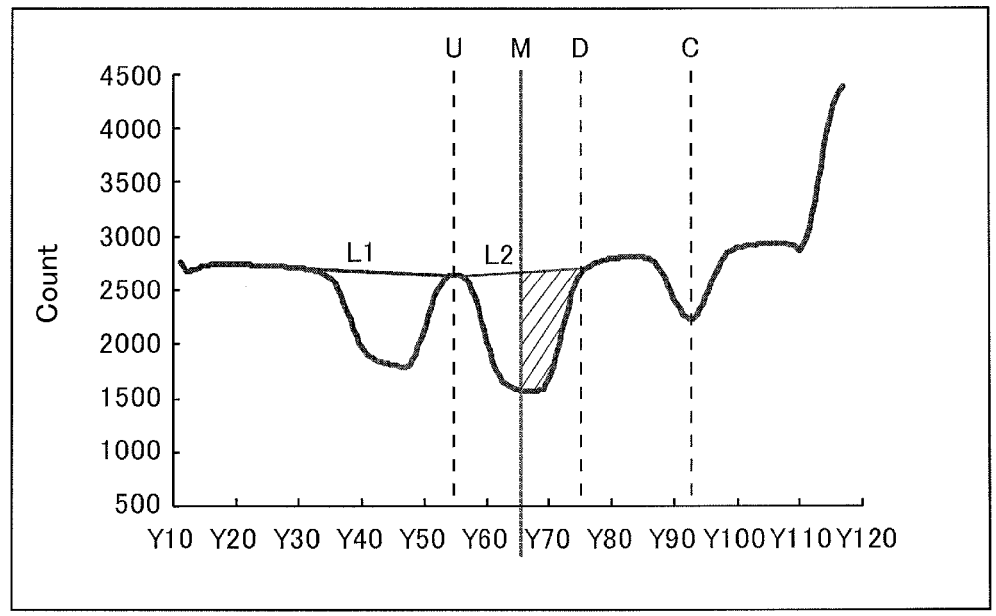
FIGS. 1A and 1B are detection charts obtained by detecting light reflected of a sample of Example 1.

In the present invention, "a prozone phenomenon" means a phenomenon in which although the actual concentration of the target component in a sample is high, it is apparently determined that no target component is present, or the concentration of the target component is low. The prozone phenomenon includes an antigen-antibody reaction and reactions in general such as those in a biochemical field other than an antigen-antibody reaction.

In the prozone phenomenon detecting method including the above-described process B of the present invention, it is preferred that generation of a prozone phenomenon is detected with reference to a previously-provided determination criterion that associates the magnitude relationship between the two or more detection results with the generation of a prozone phenomenon.

Further, it is preferred that the magnitude relationship between the detection results is at least one of a difference between the two or more detection results and a ratio between the two or more detection results.

In the case where the prozone phenomenon detecting method and the analysis method of the present invention include the above-described process A, and the prozone phenomenon detecting device and the analysis device include the section A, when the peak in the plots is on a downstream side in the sample moving direction, it can be determined that a prozone phenomenon is generated.

In the prozone phenomenon detecting method, the analysis method, the prozone phenomenon detecting device, and the analysis device of the present invention, when it is not determined in the process A that a prozone phenomenon is generated, it is preferred that the process B further is performed.

In the prozone phenomenon detecting method, the analysis method, the prozone phenomenon detecting device, and the analysis device of the present invention, it is preferred that the at least one detection portion includes two or more detection portions arranged along the sample moving direction, and in the two or more detection portions, the detection portion on the upstream side in the sample moving direction is for detecting the target component, and the detection portion on the downstream side in the sample moving direction is for detecting a prozone phenomenon.

In the prozone phenomenon detecting method, the analysis method, the prozone phenomenon detecting device, and the analysis device of the present invention, it is preferred that in the detection portion for detecting a prozone phenomenon, a prozone phenomenon is detected on the basis of detection results obtained in a region on the downstream side in the sample moving direction.

In the prozone phenomenon detecting method, the analysis method, the prozone phenomenon detecting device, and the analysis device of the present invention, it is preferred that the detection results are optical signals.

In the analysis method of the present invention, it is preferred that when generation of a prozone phenomenon is detected, the sample is determined as a false-negative.

In the prozone phenomenon detecting method, the analysis method, and the analysis device of the present invention, when the target component are antigens, the labeled substance may be labeled antibodies, and the immobilized substance may be immobilized antibodies. On the other hand, when the target component are antibodies, the labeled substance may be labeled antibodies, and the immobilized substance may be immobilized antigens. When the target component is antibodies, the antibodies as the target component are linked to the immobilized antigens, and the tip of Fab in the labeled antibodies is linked to the Fc region in the antibodies as the target component.

Next, the present invention is described in detail with examples.

In the present invention, the sample (a specimen) containing a target component is preferably liquid but is not limited thereto. In the present invention, when the sample is solid, it may be, for example, dissolved or dispersed in liquid such as a buffer solution so as to provide a solution. The buffer solution is not particularly limited, and examples thereof include a tris buffer solution, a phosphate buffer solution, an acetate buffer solution, and a borate buffer solution. In the present invention, the sample is not particularly limited, and examples thereof include: biological samples such as nasal aspirate, nasal lavage fluid, nasal swab, nasal secretion, throat swab, oral rinse, saliva, whole blood, serum, plasma, feces, urine, and cerebrospinal fluid; foods such as food substances like animals and plants and processed foods; and water collected from rivers in environmental inspection. In the present invention, when the target component is antigens or antibodies (hereinafter, also referred to as "antigens or the like"), a sample produced by extracting antigens or antibodies from the sample using an extraction fluid or the like may be used to analyze, for example. The extraction fluid is not particularly limited, and examples thereof include the above-mentioned buffer solutions. A surfactant, a stabilizing agent, an antibacterial agent, or the like may be added to the extraction fluid.

In the present invention, the target component and the sample to be applied are not at all limited. It is preferred that the present invention is applied to, for example, detections of C-reactive protein (CRP), HbA1c, TSH, FT3, FT4, hCG, HBs antigens, HBc antibodies, HCV antibodies, TY antigens, anti-streptolysin O (ASO), IV-type collagen, matrix metallo proteinase (MMP-3), PIVAK-II, α1 microglobulin, β1 microglobulin, amyloid A (SAA), elastase 1, basic fetoprotein (BFP), candida antigens, granulocyte elastase in cervical mucus, digoxin, cystatin C, a factor XIII, transferrin in urine, syphilis, hyaluronic acid, fibrin monomer complexes (SFMC), a von Willebrand factor (factor VIII-related antigens), protein S, a rheumatoid factor (RF), IgD, α1 acid glycoprotein (α1AG), α1 antitrypsin (α1AT), α2 macroglobulin, albumin (Alb), ceruloplasmin (Cp), haptoglobin (Hp), prealbumin, retinol-binding protein (RBP), β1C/β1A globulin (C3), β1E globulin (C4), IgA, IgG, IgM, β-lipoprotein (β-LP), apoprotein A-I, apoprotein A-II, apoprotein B, apoprotein C-II, apoprotein C-III, apoprotein E, transferrin (Tf), albumin in urine, plasminogen (PLG), and lipoprotein (a) (LP(a)), contained in blood.

In the present invention, when the labeled antibodies are used as the labeled substance, the labeled antibodies are not particularly limited. The labeled antibodies may be, for example, antibodies to which colored insoluble carrier particles are bound or may be antibodies to which enzymes are bound.

In the present invention, the colored insoluble carrier particles are not particularly limited, and examples thereof include colored latex particles, metal colloid particles, colored polymethyl methacrylate particles, colored polylactic acid particles, colored porous glass particles, colored silica particles, colored agarose particles, and colored dextran particles. The colored latex particles are not particularly limited, and examples thereof include blue latex particles and red latex particles. The metal colloid particles are not particularly limited, and examples thereof include gold colloid particles and platinum colloid particles. The average particle diameter of the colored insoluble carrier particles is not particularly limited. In the case of the colored latex particles, the average particle diameter is, for example, in the range from 0.05 to 5 μm, preferably from 0.1 to 1 μm. In the case of the metal colloid particles, the average particle diameter is, for example, in the range from 2 to 100 nm, preferably from 10 to 50 nm.

In the present invention, as the enzymes, those cause substrates to be colored when they react with the substrates are used, for example, and examples thereof include peroxidase, alkaline phosphatase, and β-D-galactosidase.

In the present invention, the substrates are not particularly limited as long as they are colored when they react with the enzymes. Examples thereof include 2,2'-azino-bis(3-ethylbenzothiazoline-6-sulfonic acid) (ABTS), 3,3',5,5'-tetramethylbenzidine (TMB), diaminobenzidine (DAB), 5-bromo-4-chloro-3-indolylphosphate (BCIP), 4-methylumbelliferyl-β-D-galactoside (4MUG), and 3-(2'-spiroadamantane)-4-methoxy-4-(3"-β-D-galactopyranosyl)phenyl-1,2-dioxetane (AMGPD).

In the present invention, antibodies as the above-mentioned labeled antibodies are not particularly limited as long as they specifically bind to antigens as a target component or antibodies as the same. Examples thereof include antibodies to the above-mentioned various antigens. The antibodies may be antibodies derived from biological bodies or may be antibodies obtained by artificial synthesis. Examples of the antibodies derived from biological bodies include immune globulin (Ig), antibody fragments, and chimeric antibodies. Examples of the immune globulin include IgG, IgA, IgM, IgD, IgE, and IgY. Examples of the antibody fragments include Fab, Fab', and F(ab')2. The chimeric antibodies can be, for example, humanized antibodies. In the present invention, the antibodies are not particularly limited and may be produced from serum derived from a mouse, a rabbit, a goat, a sheep, a chicken or the like by a conventionally known method, or commercially available various antibodies may be used. Further, in the present invention, any of polyclonal antibodies and monoclonal antibodies may be used as the antibodies, and they can be selected as appropriate according to the antigens or the like. The antibodies obtained by artificial synthesis can be, for example, affibodies. The affibodies are a kind of artificial antibodies obtained through screening with a library so that the affibodies can bind specifically to a target substance. The affibodies are smaller in size than antibodies, and have resistances to heat, alkali, and the like. In the present invention, antibodies as the above-mentioned immobilized antibodies are antibodies specific to antigens as a target component, and may be, for example, antibodies that can bind to the same antigens as those to which the labeled antibodies bind. The type and preparing method of the immobilized antibodies are, for example, the same as those of the labeled antibodies.

In the present invention, antigens as the above-mentioned immobilized antigens are not particularly limited and are antigens specific to antibodies as a target component. Examples thereof include the above-mentioned various antigens. In the present invention, a method for producing the immobilized antigens is not particularly limited, and can be, for example, a conventionally known method. Hereinafter the immobilized antibodies or the immobilized antigens are also referred to as "immobilized antibodies or the like".

Next, the prozone phenomenon detecting method of the present invention is described using an immunoanalytical method as an example below. However, the prozone phenomenon detecting method of the present invention is not limited by the following examples.

Figure 3A:
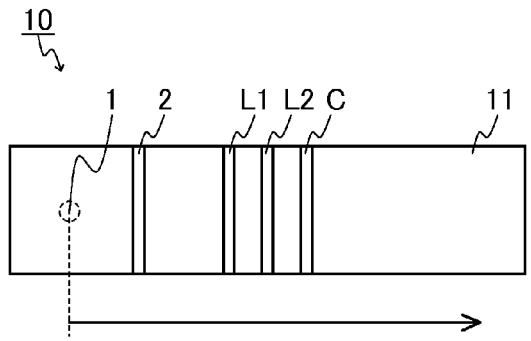
FIG. 3A is a plan view showing an example of a specimen analysis tool used in the present invention.

An example of the specimen analysis tool used in an immunoanalytical method is shown in the plan view of FIG. 3A. As shown in FIG. 3A, in this specimen analysis tool 10, a sample supplying portion 1, a reagent portion 2, a first detection portion (L1), a second detection portion (L2), and a detection portion for control (C) are on the porous base material 11 from upstream to downstream in the sample moving direction (indicated by the arrow) in this order. In this specimen analysis tool 10, a region including the first detection portion (L1), the second detection portion (L2), and the detection portion for control (C) is the detection portion. The reagent portion 2 carries labeled antibodies (for example, blue latex-labeled anti-CRP antibodies). The first detection portion (L1) is for detecting antigens (for example, CRP) as a target component, and anti-CRP antibodies are immobilized thereon. The second detection portion (L2) is for detecting a prozone phenomenon, and anti-CRP antibodies are immobilized thereon. The same antibodies with the same amount thereof are immobilized on L1 and L2. The detection portion for control (C) is, for example, a detection portion for control, on which anti-IgG antibodies are immobilized.

In the present invention, the porous base material 11 is not particularly limited as long as it has a porous structure with which a capillary action is exerted. Examples of the porous base material 11 include cellulose membranes, membranes formed of cellulose derivatives such as cellulose acetate and nitrocellulose, glass filters, and filter papers. In the present invention, the shape of the porous base material is not particularly limited, and can be, for example, rectangular or circular. In the present invention, the size of the porous base material is not particularly limited, and can be set as appropriate according to the standard of the analysis device and the like, for example.

In the specimen analysis tool of the present example, the detection portions are provided in the form of three lines extending in the width direction of the porous base material. However, the present invention is not limited thereto. The number of the detection portions can be set freely within the range from 1 to 10. Furthermore, the shape of the detection portions can be, for example, rectangular or circular, in addition to the line form.

Figure 3B:
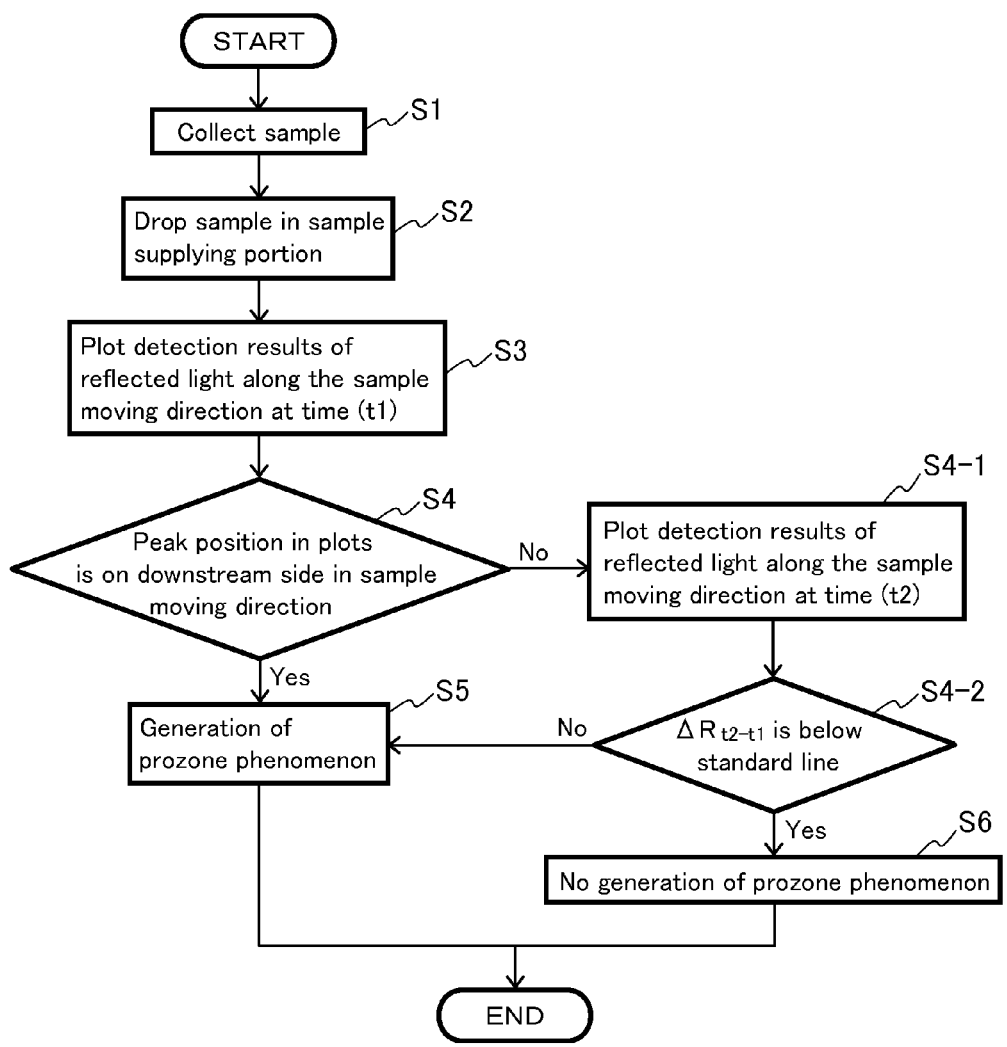
FIG. 3B is a flowchart showing an example of a method for detecting a prozone phenomenon of the present invention.

An example of a prozone phenomenon detecting method in an immunoanalytical method using the specimen analyzing tool of the present example is described with reference to FIGS. 3A and 3B.

(Prozone Phenomenon Detection in Process A)

A serum (a sample) is collected (Step S1). Next, the sample is dropped on the sample supplying portion 1 (Step S2), so that the sample is supplied to the reagent portion 2 and dissolves the labeled antibodies carried by the reagent portion 2. When the sample contains antigens as a target component, the labeled antibodies bind to the antigens through an antigen-antibody reaction, thereby forming antigen-labeled antibody conjugates. Then, the antigen-labeled antibody conjugates are developed in the porous base material and bind to the immobilized antibodies in the detection portion, thereby forming complexes. With the formation of the complexes, the first detection portion (L1), the second detection portion (L2), and the detection portion for control (C) are colored by the label.

Next, at the time point (t1), reflected light indicating the presence or absence of the coloring and the degree of the same in the detection portion is detected. Specifically, first, provided is a chart in which detection results of the reflected light obtained in the detection portion are plotted along the sample moving direction (indicated by the arrow) (Step S3). Then, a valley-shaped peak appearing in the vicinity of coordinates of the detection portion for control (C) is detected. In the case where this valley-shaped peak is not detected, it is regarded that the sample and the labeled antibodies are not moving normally, so that it is determined that a measurement cannot be performed. Thereafter, two valley-shaped peaks appearing in the vicinity of coordinates of the first detection portion (L1) and the second detection portion (L2), respectively, are detected. The mountain-shaped peak appearing at the border between the two valley-shaped peaks is taken as the border between the first detection portion (L1) and the second detection portion (L2). The coordinate at this border is taken as the coordinate at the end on the upstream side of the second detection portion (L2). On the other hand, the coordinate that is the predetermined value more than the coordinate at the border toward the downstream side is taken as the coordinate at the end on the downstream side of the second detection portion (L2). A plot of the detection value at the coordinate that is at the end on the upstream side is connected to a plot of the detection value at the coordinate that is at the end on the downstream side with a line segment. A region enclosed in the line segment and the plots forming a valley shape is taken as a peak area of the entire second detection portion (L2). In the present invention, generation of a prozone phenomenon is detected from a shape (a position of a peak) formed by plots of the detection portion. It is preferred that whether or not a prozone phenomenon is generated is determined on the basis of whether the peak is in the first half (on the upstream side) of the peak area of the entire second detection portion (L2) or in the latter half (on the downstream side) of the same. Specifically, first, it is determined whether or not the peak is in the latter half (on the downstream side) of the peak area of the entire second detection portion (L2) (Step S4). When the peak is not on the downstream side (No), generation of a prozone phenomenon is detected in the same manner as the detection of a prozone phenomenon in the process B described below. When the peak is on the downstream side (Yes), it is determined that a prozone phenomenon is generated (Step S5). For example, in the second detection portion (L2), the peak area is divided into two of "the first half" and "the latter half" by the standard line drawn through the center of the line segment. Next, in the respective areas, the minimum values (the first half: L2*f*–min, the latter half: L2*l*–min) in plots of the detection values are determined. When the minimum values satisfy L2*f*–min≥L2*l*–min, it is determined that a prozone phenomenon is generated.

Whether or not the peak is in the latter half (on the downstream side) of the peak area of the entire second detection portion (L2) is determined with dividing the peak area into two areas by the standard line drawn through the center of the line segment above. However, it is not limited to this. The standard line may be drawn through the point one third of the ling segment on the downstream side, and the upstream side and the downstream side may be defined by the standard line as a border. The position provided with the standard line can be decided according to, for example, detection properties of the target component, the size of the detection portion, the distance between the sample supplying portion and the detection portion, and the time required for the measurement.

In the case where there are plural detection portions, it is possible that the peak height of the detection portion on the upstream side is compared with that of the detection portion on the downstream side, and when the peak height of the detection portion on the downstream side is higher, it is determined that a prozone phenomenon is generated.

As a cause of a prozone phenomenon, it is considered that since antigens with an amount more than an amount capable of reacting with labeled antibodies carried by the reagent portion are present excessively in a sample, antigens that have not reacted with the labeled antibodies flow into the detection portion and react with antibodies immobilized on the detection portion. In this case, the antigens that have not reacted with the labeled antibodies mask the antibodies immobilized on the detection portion. Thus, antigens that have reacted with the labeled antibodies, which flow into the detection portion later cannot react with the antibodies immobilized on the detection portion, whereby a developed color becomes pale. This phenomenon is generated on the upstream side of the detection portion more apparent than on the downstream side thereof. Therefore, when a peak is present in the latter half of the detection portion, it can be determined that a prozone phenomenon is generated.

An example in which a prozone phenomenon is detected in the second detection portion (L2) is shown above. However, a prozone phenomenon may be detected in the first detection portion (L1). When the specimen analysis tool includes three or more detection portions, the detection may be performed in any of them.

(Detection of Prozone Phenomenon in Process B)

When it is determined that a prozone phenomenon is not generated by the detection of prozone phenomenon in the process A, previously-obtained detection results of reflected light indicating the presence or absence of the coloring and the degree of the same in the detection portion at the time point (t2) that is prior to the time point (t1) are plotted in the same manner as at the time point (t1) (Step S4-1). Then, a prozone phenomenon is detected on the basis of the amount of change between a reflectance at the time point (t2) and a reflectance at the time point (t1) in the second detection portion (L2), for example. In the case, a prozone phenomenon may be detected on the basis of a peak area of the entire second detection portion (L2), and, for example, it is preferred that the peak area is divided into two at the coordinate drawn through the center of the line segment, and a prozone phenomenon is detected on the basis of a region on the downstream side of the second detection portion (L2). First, with respect to the detection results at the time (t1) in a region on the downstream side of the second detection portion (L2), count values are converted into ratios (%) of them to the line segment, respectively, and the ratios are integrated, so that a reflectance $R_{t1}$ (%) is determined. Similarly, reflected light at the time point (t2) in the detection portion is detected, and a reflectance $R_{t2}$ (%) is determined. The time from starting the detection to the time point (t1) is not particularly limited, and is, for example, in the range from 5 to 20 minutes, preferably from 5 to 15 minutes, and more preferably from 8 to 12 minutes. The difference in time (t1–t2) between the time point (t1) and the time point (t2) also is not particularly limited, and is, for example, in the range from 2 to 8 minutes, preferably from 3 to 7 minutes, and more preferably from 4 to 6 minutes. Generation of a prozone phenomenon is detected on the basis of the difference between obtained two reflectances ($\Delta R_{t2-t1}$ (%)=$R_{t2}-R_{t1}$). The detections of reflected light and the determinations of reflectance are not limited to the detections and determinations at the time point (t1) and the time point (t2), and may be performed three or more times. Further, the detection of reflected light may be performed every one minute with time, and the average value of three detection results at the time point (t2)–1 minute, at the time point (t2), and at the time point (t2)+1 minute may be taken as a detection result at the time (t2).

It is preferred that generation of a prozone phenomenon is detected with reference to a previously-provided determination criterion that associates the difference in reflectance with the generation of a prozone phenomenon. As the determination criterion, a standard line in a graph obtained by plotting the relationship between the difference in reflectance and the generation of a prozone phenomenon and a table showing the relationship between the same can be used. When the standard line in a graph obtained by plotting the relationship between the difference in reflectance and the generation of a prozone phenomenon is used, a border line may be provided by a least-squares method and is used as the standard line. Specifically, first, whether or not the difference in reflectance ($\Delta R_{t2-t1}$) is below the standard line is determined (Step S4-2). When it is below the standard line (Yes), it is determined that a prozone phenomenon is generated (Step S5). When it is not below the standard line (No), it is determined that a prozone phenomenon is not generated (Step S6).

The detection of generation of a prozone phenomenon may be, in addition to or as substitute for the detection on the basis of the difference in reflectance, detection on the basis of the ratio between reflectances or detection on the basis of the magnitude relationship between the reflectances other than the difference in reflectance and the ratio between the reflectances. Further, in the present example, the detection of a label was performed using a reflectance that is an optical signal. However, the detection may be performed using a transmittance, an absorbance, or the like.

When the target component can be oxidized, the detection of generation of a prozone phenomenon may be, in addition to or as substitute for the above-mentioned detection on the basis of the magnitude relationship between the reflectances according to the coloring of labeled antibodies, detection on the basis of the magnitude relationship between oxidization current values. In this case, as the labeled antibodies or the like, antibodies or antigens to which oxidoreductases have been bound are used, and an electron acceptor and an electrode (a cathode and an anode) are arranged in the detection portion. The oxidoreductases may be those can oxidize the target component. In the case of using such the oxidoreductases, generation of a prozone phenomenon can be detected as follows, for example. That is, in the second detection portion (L2), while the target component is oxidized by a catalyst reaction of the oxidoreductases, the electron acceptor is reduced. The electron acceptor thus reduced is re-oxidized by an electrochemical technique. An oxidation current value obtained by this re-oxidization corresponds to the amount of the target component, whereby the target component can be indirectly subjected to a quantitative determination by measuring the current value. The electrode is not particularly limited, and examples thereof include a gold electrode, a carbon electrode, and a silver electrode. In the specimen analysis tool, the electrode is an optional component. The electrode may be, for example, arranged in the detection portion at the time of using the specimen analysis tool.

An embodiment in which when it is determined that a prozone phenomenon is not generated by the detection of a prozone phenomenon in the process A, the detection of a prozone phenomenon in the process B further is performed is described above. However, in the present invention, only the process A or the process B in the processes A and B can be employed to detect a prozone phenomenon.

Next, the analysis method of the present invention is described. As mentioned above, the analysis method of the present invention includes an analyzing step and the prozone phenomenon detecting step. The analyzing step is performed using a specimen analysis tool. The specimen analysis tool is the same as the one used in the prozone phenomenon detecting method of the present invention. The prozone phenomenon detecting step is performed by the prozone phenomenon detecting method of the present invention.

In the analyzing method of the present invention, it is preferred that when generation of a prozone phenomenon is detected in the prozone phenomenon detecting step, it is regarded that the analysis of the target component in the sample is not determined correctly, so that the sample is determined as a false-negative. With the determination as a false-negative, it is distinguished from a negative, whereby an analysis can be performed more accurately. Further, generation of a prozone phenomenon is detected, whereby there is no need to dilute a sample and re-perform an analysis.

Next, the prozone phenomenon detecting device of the present invention is described. As mentioned above, the prozone phenomenon detecting device of the present invention is used in the prozone phenomenon detecting method of the present invention. The device includes: a section for obtaining detection results in the detection portion; and at least one of the following sections A and B. The section A is a section for detecting generation of a prozone phenomenon on the basis of a position of a peak in plots obtained by plotting the detection results along the sample moving direction. The section B is a section for detecting a label at two or more different time points and detecting generation of a prozone phenomenon on the basis of a magnitude relationship between two or more detection results thus obtained.

In the case where reflected light is detected in the prozone phenomenon detecting method of the present invention as mentioned above, the obtaining section includes a light source portion and a light receiving portion. The light source portion emits light, so that in the specimen analysis tool 10, the porous base material including the first detection portion (L1), the second detection portion (L2), and the detection portion for control (C) is irradiated with the light, and the light receiving portion detects reflected light. The light source portion includes, for example, a light emitting diode (LED), a semiconductor laser diode (LD), or the like. The light receiving portion includes, for example, a photodiode, a photomultiplier tube (photomul), a CCD (charge coupled device) image sensor, or the like.

When oxidation current values are detected in the prozone phenomenon detecting method of the present invention as mentioned above, the obtaining section includes, for example, an electric power supply and an ammeter. First, the electrode (cathode and anode) is connected to the electric power supply, and the ammeter is arranged between the electrode and the electric power supply. Then, a voltage is applied the electrode. After the sample reaches to the second detection portion (L2), the oxidation current values are detected. At the end, the target component is subjected to a quantitative determination based on the oxidization current values.

The obtaining section may be a part of the prozone phenomenon detecting device of the present invention or may be external equipment.

The detecting section includes a central processing unit (CPU), a memory, an input terminal, and an output terminal. Examples of the input terminal include a keyboard and a touch panel. Examples of the output terminal include a display and a printer. The whole of the detecting section may be arranged in the main body of the prozone phenomenon detecting device, or the whole or a part of the detecting section may be arranged outside of the main body of the device. For example, the detecting section may be provided in a personal computer (PC). The above-mentioned various determination criteria used in the detecting section may have been stored in a memory previously and referred to at the time of detection, or they may be entered into the CPU through the input terminal and referred to. The prozone phenomenon detection results are output to the output terminal.

Next, the analysis device of the present invention is described. As mentioned above, the analysis device includes: an analysis section; and a prozone phenomenon detecting section. The analyzing section detects a target component by detecting a complex of the target component, a labeled substance, and an immobilized substance through detection of a label of the labeled substance in a detection portion of a specimen analysis tool, and the prozone phenomenon detecting section is the prozone phenomenon detecting device of the present invention.

The analyzing section includes a central processing unit (CPU), a memory, an input terminal, and an output terminal. Examples of the input terminal include a keyboard and a touch panel. Examples of the output terminal include a display and a printer. The whole of the detecting section may be arranged in the main body of the analysis device, or the whole or a part of the detecting section may be arranged outside of the main body of the device. For example, the analyzing section may be provided in a personal computer (PC). The target component detection results are output to the output terminal.

The present invention is described in more detail using the examples below. However, the present invention is not limited thereto.

EXAMPLES

Example 1

Samples containing CRP at the various concentration are prepared, and specific examples of a detection of generation of a prozone phenomenon in an immunochromatography method using a specimen analysis tool and a determination criterion that can be used suitably in a detection of a prozone phenomenon including the method B are described below.

(CRP Specimen)

Sera collected from plural subjects and healthy subjects were used as the respective samples. CRP concentrations of the respective sera were previously determined by a latex immunoturbidimetric method. On the basis of the CRP concentrations, the respective sera were classified into a sample in which a normal antigen-antibody reaction occurs and a sample in which a prozone phenomenon is generated. Specifically, samples at CRP concentrations of 0.6 mg/100 mL, 2.5 mg/100 mL, and 6.5 mg/100 mL, respectively, were classified as a sample in which a normal antigen-antibody reaction occurs. Samples at a CRP concentration of 25 mg/100 mL or more were classified as a sample in which a prozone phenomenon is generated.

(Specimen Analysis Tool)

Figure 4A:
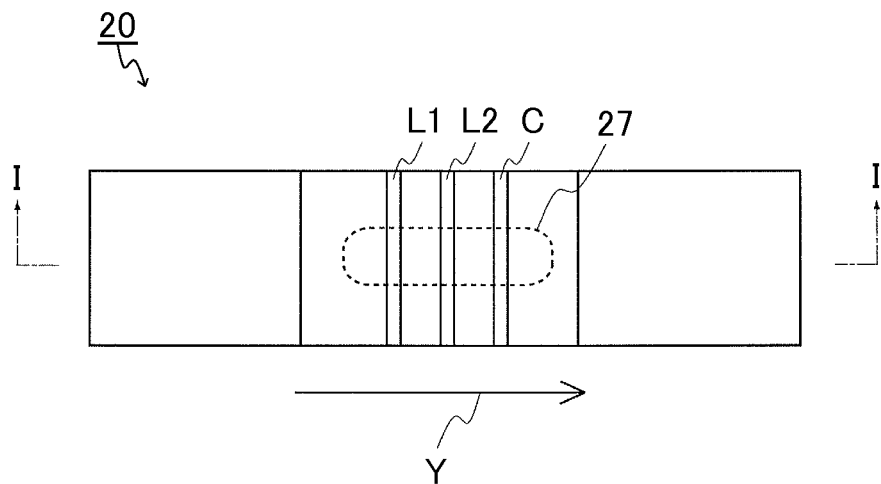
FIG. 4A is a plan view showing another example of a specimen analysis tool used in the present invention.
Figure 4B:
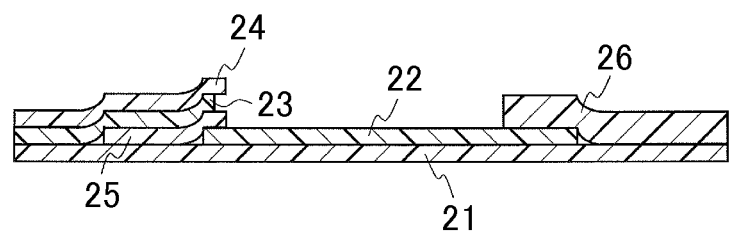
FIG. 4B is a sectional view taken along the line I-I of the specimen analysis tool shown in FIG. 4A.
Figure 4C:
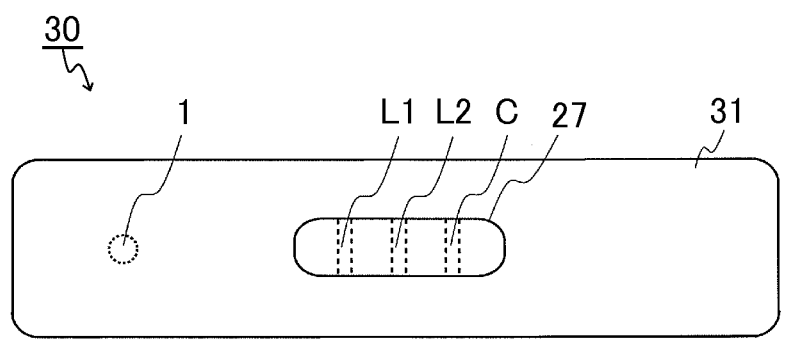
FIG. 4C is a plan view of a specimen analysis chip in which the specimen analysis tool is contained in a case body.
Figure 5:
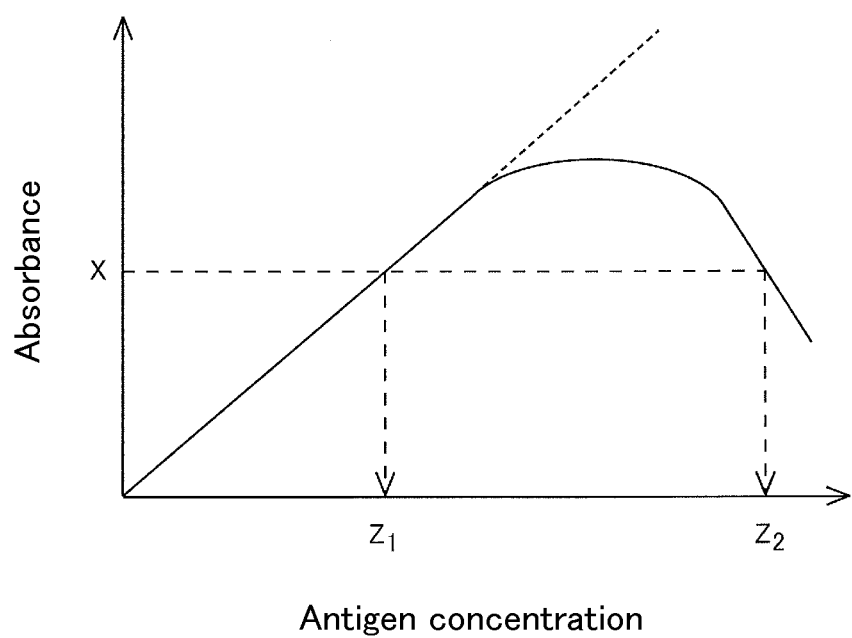
FIG. 5 is an illustration explaining a prozone phenomenon.

As a specimen analysis tool for CRP measurement, "Spot Chem i-Line CRP" (product name) (manufactured by ARKRAY, Inc.) was used. An overview of this specimen analysis tool is shown in FIGS. 4A to 4C. FIG. 4A is a plan view of the specimen analysis tool 20. FIG. 4B is a sectional view taken along the line I-I of FIG. 4A. FIG. 4C is a plan view of a specimen analysis chip 30 in which the specimen analysis tool 20 is contained in a case body 31. In FIGS. 4A to 4C, the portions identical to those in FIG. 3A are given the same numbers and symbols. The specimen analysis tool 20 includes an upper base plate (not shown), the lower base plate 21, the porous body for detection 22, the two porous bodies for sample 23 and 24, the porous body for labeled antibody 25, carrying blue latex-labeled anti-CRP antibodies, and the porous body for absorption 26, absorbing an excess amount of specimen. The porous body for detection 22 is laminated on the center of the lower base plate 21 in the longitudinal direction thereof. The porous body for labeled antibody 25, carrying blue latex-labeled anti-CRP antibodies is laminated on one end (on left side of FIG. 4B) of the porous body for detection 22. The two layers of the porous bodies for sample 23 and 24 are laminated on the porous body for labeled antibody 25. The porous body for absorption 26 is laminated on the other end (on right side of FIG. 4B) of the porous body for detection 22. Based on the sample moving direction, a side (the left side of FIG. 4B) of the porous body for detection 22, on which porous bodies for sample 23 and 24 are laminated is taken as upstream, and a side (the right side of FIG. 4B) of the same, on which the porous body for absorption 26 is laminated is taken as downstream. The porous body for detection 22 includes, from upstream in this order, the first detection portion (L1) and the second detection portion (L2), on which anti-CRP antibodies have been immobilized and the detection portion for control (C), on which anti-IgG antibodies has been immobilized. A region including the first detection portion (L1), the second detection portion (L2), and the detection portion for control (C) is a detection portion 27. The upper base plate (not shown) is arranged so as to cover the various porous bodies laminated on the lower base plate 21. Note here that the upper base plate is provided with a through hole at the portion corresponding to the sample supplying portion of the porous body for sample 24, and the portions of the upper base material, corresponding to the first detection portion (L1), the second detection portion (L2), and the detection portion for control (C), respectively, are exposed. The distance between the center of the through hole and that of the first detection portion (L1) is 30 mm. The distance between the center of the through hole and that of the second detection portion (L2) is 33.5 mm. The distance between the center of the through hole and that of the detection portion for control (C) is 38 mm.

(Optical Signal Measurement)

5 μL of each sample was added to the specimen analysis tool, and thereafter, within one minute from the addition, the specimen analysis tool was set in a reflected light measuring device (SPOTCHEM (registered trademark) IL, product name, manufactured by ARKRAY, Inc.). Then reflected light indicating the presence or absence of coloring and the degree of the same was detected. The reflected light was detected once every one minute with time, assuming that the time at which the specimen analysis tool was set in the device is a detection start time (0 second). The detection of reflected light was conducted with respect to the detecting portion 27 in the sample moving direction.

Figure 1B:
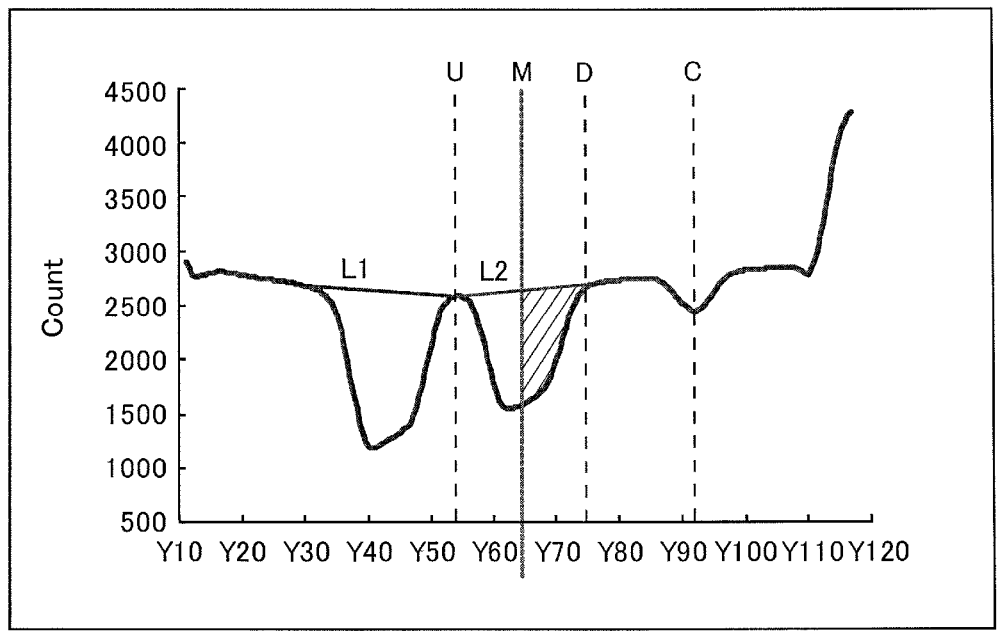

With respect to a sample at the CRP concentration of 60 mg/100 mL and a sample at the CRP concentration of 6.5 mg/100 mL among the various samples, detection charts obtained through the detection of reflected light after 10 minutes from the detection start time are shown in FIGS. 1A and 1B, respectively. FIG. 1A shows a result with respect to a sample at a CRP concentration of 60 mg/100 mL, and FIG. 1B shows a result with respect to a sample at a CRP concentration of 6.5 mg/100 mL. In both the FIGS. 1A and 1B, the X axis indicates a coordinate extending from upstream toward downstream in the detection portion of the specimen analysis tool, and one scale indicates about 0.167 mm. In both the FIGS. 1A and 1B, the Y axis indicates a value (unit: count) detected by the reflected light measuring device. The lower the value, the higher the degree of coloring, i.e., a reflectance is low.

In the detection chart of FIG. 1A, the peak in plots is on the downstream side in the sample moving direction, so that it is determined that "a prozone phenomenon is generated" in the prozone phenomenon detection by the process A. In the detection chart of FIG. 1B, the peak in plots is on the upstream side in the sample moving direction, so that it is not determined that "a prozone phenomenon is generated" in the prozone phenomenon detection by the process A.

Next, from detection results of the respective samples in the second detection portion, a reflectance after 5 minutes from the start of the detection, a reflectance after 10 minutes from the same, and a degree of increase between the reflectance after 5 minutes and the reflectances after 10 minutes were determined. Specifically, with respect to each sample, a chart showing a relationship between the coordinates and the detection values, which is exemplified in FIGS. 1A and 1B was provided, and then a valley-shaped peak (C) appearing in the vicinity of coordinates (Y80 to Y110) of the detection portion for control was detected. In the case where this valley-shaped peak was not detected, it was regarded that the sample and blue latex-labeled anti-CRP antibodies were not moving normally, so that it was determined that a measurement cannot be performed and was excluded from the target to be evaluated. Thereafter, two valley-shaped peaks appearing in the vicinity of coordinates (Y30 to Y80) of the first detection portion (L1) and the second detection portion (L2) were detected. The mountain-shaped peak appearing at the border between the two valley-shaped peaks was decided as the border between the first detection portion (L1) and the second detection portion (L2). The coordinate at this border was decided as the coordinate (U) at the end on the upstream side of the second detection portion (L2). On the other hand, the coordinate that is Y20 more than the coordinate at the border toward the downstream side was decided as the coordinate (D) at the end on the downstream side of the second detection portion (L2). A plot of the detection value at the coordinate (U) that is at the end on the upstream side was connected to a plot of the detection value at the coordinate (D) that is at the end on the downstream side with a line segment. A region enclosed in the line segment and the plots forming a valley shape is a peak area of the entire second detection portion (L2). In the present example, the coordinate (M) drawn through the center of the line segment was decided, and results in a region (shadow area in both FIGS. 1A and 1B) on the downstream side of the second detection portion (L2) were used. With respect to the results in a region on the downstream side of the second detection portion (L2), count values were converted into ratios (%) of them to the line segment, respectively, and the ratios were integrated, so that a reflectance (%) was determined. Similarly, with respect to each sample, a reflectance ($R_5$) after 5 minutes and a reflectance ($R_{10}$) after 10 minutes in the region on the downstream side of the second detection portion (L2) were calculated, and further the difference ($\Delta R_{5-10}$) between the reflectance ($R_5$) after 5 minutes and the reflectance ($R_{10}$) after 10 minutes was calculated by the following formula:

$$\Delta R_{5-10}(\%) = R_5 - R_{10}.$$

As "reflectance after 5 minutes", a value calculated from a detection value after 5 minutes from the start of the detection may be used, or "an average value calculated from the detection values after 4 minutes, 5 minutes, and 6 minutes, respectively" also can be used, for example.

Figure 2:
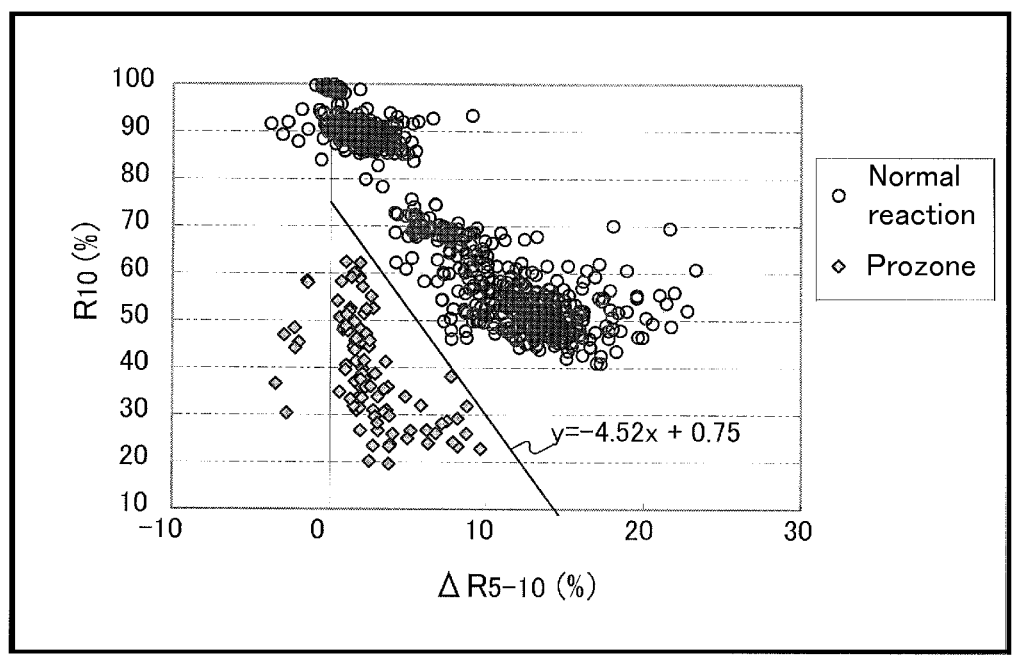
FIG. 2 is a graph showing a relationship between the reflectance ($R_{10}$) after 10 minutes and the difference in reflectance ($\Delta R_{5-10}$), in a region on the downstream side of the second detection portion in Example 1.

These results are shown in FIG. 2. FIG. 2 is a graph showing a relationship between the reflectance ($R_{10}$) after 10 minutes and the difference in reflectance ($\Delta R_{5-10}$). In FIG. 2, the X axis indicates the difference in reflectance ($\Delta R_{5-10}$), while the Y axis indicates a reflectance ($R_{10}$) after 10 minutes. ○ indicates the sample in which a normal antigen-antibody reaction can be performed. ◆ indicates a sample with the possibility of generating a prozone phenomenon. As shown in FIG. 2, plots of the sample (◆) with possibility of generating a prozone phenomenon crowded on the lower left side of the graph, whereas plots of the sample (○) in which a normal antigen-antibody reaction can be performed crowded on the upper right side of the graph. An analysis was performed to divide both the groups of plots, so that the formula, Y=−4.52x+0.75, was obtained as shown in FIG. 2. By the use of calibration curve based on this formula, even though a CRP concentration of a sample is unknown, the presence or absence of generation of a prozone phenomenon can be determined on the basis of the reflectance ($R_{10}$) after 10 minutes and the difference in reflectance ($\Delta R_{5-10}$).

INDUSTRIAL APPLICABILITY

As above, according to the present invention, it becomes possible to easily detect generation of a prozone phenomenon even when a conventional specimen analysis tool is used and becomes possible to efficiently perform examinations using an immunochromatography method or the like. The prozone phenomenon detecting method, the analysis method, the prozone phenomenon detecting device, and the analysis device of the present invention are applicable to fields of clinical examinations, biochemical examinations, medical researches, and the like, uses thereof are not limited, and they are applicable to wide range of field.

EXPLANATION OF REFERENCE NUMERALS 1 sample supplying portion
2 reagent portion
10, 20 specimen analysis tool
11 porous base material
21 lower base plate
22 porous body for detection
23, 24 porous body for sample
25 porous body for labeled antibody
26 porous body for absorption
27 detection portion
30 specimen analysis chip
31 case body
L1 first detection portion
L2 second detection portion
C detection portion for control

The invention claimed is:

1. A method for detecting a prozone phenomenon using a specimen analysis tool containing substances that specifically bind to a target component contained in a sample, the specimen analysis tool comprising:
   a porous base material;
   a sample supplying portion;
   a reagent portion; and
   at least one detection portion,
   the sample supplying portion, the reagent portion, and the detection portion being arranged on the porous base material from upstream to downstream in a sample moving direction in this order,
   wherein
   the reagent portion contains a labeled substance that specifically binds to the target component,
   the detection portion contains an immobilized substance that specifically binds to the target component, and
   the target component is detected by detecting a complex of the target component, the labeled substance, and the immobilized substance through detection of a label of the labeled substance in the detection portion,
   wherein the prozone phenomenon detecting method comprises a process A in which results of detection of the label are plotted along the sample moving direction, and a position of a peak thus generated is determined at its apex at one time point in the detection portion, and
   wherein when the apex of the peak appears in the latter half of the total peak area in the sample moving direction, a prozone phenomenon is present.

2. The prozone phenomenon detecting method according to claim 1, wherein when it is not determined after performing process A that a prozone phenomenon is present, a process B is then performed in which the label is detected at two or more different time points in the detection portion, and generation of a prozone phenomenon is detected on the basis of a magnitude relationship between two or more detection results thus obtained, with reference to a previously provided determination criterion that associates the magnitude relationship between the two or more detection results with the generation of the prozone phenomenon.

3. The prozone phenomenon detecting method according to claim 1, wherein
   the at least one detection portion comprises two or more detection portions arranged along the sample moving direction, and
   in the two or more detection portions, the detection portion on the upstream side in the sample moving direction is for detecting the target component, and the detection portion on the downstream side in the sample moving direction is for detecting a prozone phenomenon.

4. The prozone phenomenon detecting method according to claim 3, wherein in the detection portion for detecting a prozone phenomenon, a prozone phenomenon is detected on the basis of detection results obtained in a region on the downstream side in the sample moving direction.

5. The prozone phenomenon detecting method according to claim 1, wherein the results of the detection appear as optical signals.

6. The prozone phenomenon detecting method according to claim 1, wherein
   the target component is an antigen,
   the labeled substance is a labeled antibody, and
   the immobilized substance is an immobilized antibody.

7. The prozone phenomenon detecting method according to claim 1, wherein
the target component is an antibody,
the labeled substance is a labeled antibody, and
the immobilized substance is an immobilized antigen.

8. An analysis method comprising:
an analyzing step; and
a prozone phenomenon detecting step,
wherein
the analyzing step is performed using a specimen analysis tool containing substances that specifically bind to a target component contained in a sample, the specimen analysis tool comprising:
a porous base material;
a sample supplying portion;
a reagent portion; and
at least one detection portion,
the sample supplying portion, the reagent portion, and the detection portion being arranged on the porous base material from upstream to downstream in a sample moving direction in this order,
wherein
the reagent portion contains a labeled substance that specifically binds to the target component,
the detection portion contains an immobilized substance that specifically binds to the target component, and
the target component is detected by detecting a complex of the target component, the labeled substance, and the immobilized substance through detection of a label of the labeled substance in the detection portion,
wherein the prozone phenomenon detecting method comprises a process A in which results of detection of the label are plotted along the sample moving direction, and a position of a peak thus generated is determined at its apex at one time point in the detection portion, and
wherein when the apex of the peak appears in the latter half of the total peak area in the sample moving direction, a prozone phenomenon is present.

9. The analysis method according to claim 8, wherein when a prozone phenomenon is detected in the prozone phenomenon detecting step, the sample is determined as a false-negative.

10. The prozone phenomenon detecting method according to claim 2, wherein
the magnitude relationship between the detection results is at least one of a difference between the two or more detection results and a ratio between the two or more detection results.

\* \* \* \* \*